United States Patent [19]

Wong et al.

[11] 4,150,049

[45] Apr. 17, 1979

[54] ESTERS OF AROMATIC SULFONIC ACIDS

[75] Inventors: Show-Chu Wong, Riverhead; Elliott Shaw, Shoreham, both of N.Y.

[73] Assignee: The Government of the United States, Washington, D.C.

[21] Appl. No.: 855,018

[22] Filed: Nov. 22, 1977

Related U.S. Application Data

[60] Continuation of Ser. No. 711,569, Aug. 4, 1976, abandoned, which is a division of Ser. No. 629,133, Nov. 5, 1975, Pat. No. 4,001,087, which is a continuation of Ser. No. 513,565, Oct. 10, 1974, abandoned.

[51] Int. Cl.² ........................................... C07C 143/68
[52] U.S. Cl. ................................................ 260/456 A
[58] Field of Search ..................................... 260/456 A

[56] References Cited

PUBLICATIONS

Shaw, Bayer–Symposium V "Proteinase Inhibitors" pp. 531–540 (1974).
Shaw, Report 1973, BNL–18364.
Wong et al., Archives of Biochem. & Biophy., 161, 536 (1974).

*Primary Examiner*—Nicky Chan
*Attorney, Agent, or Firm*—Holman & Stern

[57] ABSTRACT

Novel esters of aromatic sulfonic acids are disclosed. The specific esters are nitrophenyl p- and m-amidinophenylmethanesulfonate. Also disclosed is a method for specific inactivation of the enzyme, thrombin, employing nitrophenyl p-amidinophenylmethanesulfonate.

4 Claims, 4 Drawing Figures

ESTERS OF AROMATIC SULFONIC ACIDS

The invention described herein was made in the course of work under a grant or award from the Department of Health, Education and Welfare.

This is a continuation of application Ser. No. 711,569, filed Aug. 4, 1976, now abandoned; which in turn is divisional of Ser. No. 629,133, filed Nov. 5, 1975, now U.S. Pat. No. 4,001,087, issued Jan. 4, 1977, which in turn is a continuation of application Ser. No. 513,565, filed Oct. 10, 1974, now abandoned.

BACKGROUND AND SUMMARY OF THE INVENTION

The present invention relates to esters of aromatic sulfonic acids and the use of such acids in the inhibition of proteolytic enzymes. More particularly, the present invention relates to esters of aromatic sulfonic acids containing an amidino group and the use of such esters in the inhibition and inactivation of enzymes such as thrombin.

In the study of enzyme behavior, affinity labeling has provided an approach to identifying functional groups in enzymes that has had wide applicability. The success of this method depends on devising reagents which are substrate-like in structure, leading to an enzyme-reagent complex with subsequent covalent bond formation. The newly formed bond must be stable enough to permit structural study by standard methods of protein chemistry.

It has been appreciated that the same approach might be of value in arriving at therapeutically useful agents since inactivation with covalent bond formation would confer maximal effectiveness to inhibitors whose selectively arises from substrate-like structural features.

With specific regard to the enzyme, thrombin, this is a proteolytic enzyme which catalyzes the conversion of fibrinogen to fibrin and thus is essential in the clotting mechanism of blood. It is present in the blood in the form of prothrombin under normal conditions; when bleeding begins, the prothrombin is converted to thrombin, which in turn activates the formation of fibrin. Thus, the inactivation of thrombin would result in an anticoagulant action which would be useful in various therapeutic treatments and studies.

With the goal of obtaining a reagent capable of discriminating among trypsin-like enzymes and inactivating one of them, nitrophenyl m- and p-amidinophenylmethanesulfonate have been synthesized, in accordance with the present invention, such compounds having specific use as potential affinity labels. Both compounds were found to be competitive inhibitors of trypsin, thrombin, plasmin, chymotrypsin, and plasma kallikrein. However, in the case of thrombin alone, the p-isomer achieves a covalent modification irreversibly inactivating the enzyme. The results obtained, as discussed hereinafter, demonstrate the selectivity possible with such an active site-directed reagent even among enzymes with homologous active centers.

A number of physiologically important proteolytic enzymes appear to be derived from trypsin by gene duplication. Several of these which are liberated in plasma by zymogen activation such as thrombin, plasmin, and kallikrein have key roles in coagulation, fibrinolysis, and permeability. The ability to selectively inactivate one of these or other trypsin-like protease would be of therapeutic value. Since these enzymes have the hydrolytic mechanism common to serine proteases and a specificity site for a basic amino acid side chain, it seemed likely that their physiological selectivity in proteolysis would depend on recognition of larger regions of their normal macromolecular substrates. Correspondingly, it seemed unlikely that small reagents comparable in size to a single basic amino acid could selectively inhibit one of these trypsin-like enzymes and not the others.

On the other hand, it has been observed that esters of p-guanidinobenzoic acid, an analog of lysine and arginine, form relatively stable acyl-enzyme derivatives with trypsin-like enzymes. Since thrombin and plasmin differ in the duration of their inactivation as p-guanidinobenzoyl enzymes, it appeared that there are kinetic differences between thrombin and plasmin that may be exploited for selective inactivation by this type of quasi-substrate. In general, the results supported the earlier impression that the immediate region of the hydrolytic center of thrombin is more flexible than that of plasmin, i.e., less likely to adopt an acyl-enzyme configuration which excludes the productive approach of a water molecule essential for deacylation. The latter situation appears to explain the stability of one acyl-enzyme, indoleacryloyl-chymotrypsin, and is considered as probably applying to other relatively rigid acyl residues. Since an adequately stable acyl-thrombin was not found, attention was turned to the possibility of selective formation of a sulfonyl thrombin derivative by affinity labeling since prior experience indicates that this type of serine protease derivative is most stable to hydrolysis. However, in such a case, selectivity among trypsin homologs would have to be achieved by differences in sulfonylation rather than in desulfonylation.

The most favorable result would therefore be a qualitative difference in which the reagent, although complexing with a variety of trypsin-like enzymes as expected in the affinity labeling approach, would achieve covalent modification with only one member of the group, presumably due to small differences in geometry in the region of the active center that provide the correct orientation for sulfonylation of the active center only with a single member of the group.

In accordance with the present invention, nitrophenyl p- and m-amidinophenylmethanesulfonate, hereinafter sometimes referred to as the p- and m-isomers, have been prepared. These compounds have been found to be effective inhibitors of thrombin, with the p-isomer providing specific inactivation of this enzyme.

BRIEF DESCRIPTION OF THE DRAWINGS

The features of the compounds and method of the present invention will be more clearly understood from the following detailed description, taken in conjunction with the accompanying drawings, wherein.

DESCRIPTION OF THE PREFERRED EMBODIMENTS

In accordance with the present invention, nitrophenyl m- and p-amidinophenylmethanesulfonate were prepared, and these compounds were examined for their properties related to inhibition and inactivation of specific enzymes. With regard to the enzymes employed, bovine β-trypsin and thrombin were chromatographically purified by known procedures. Human plasminogen was purified from Cohn fraction III and activated with streptokinase. Human plasma kallikrein was purified about 1000-fold from activated Cohn fraction IV, by affinity chromatography. Human thrombin was prepared by the method of Miller and Copeland. Bovine chymotrypsin three times crystallized was also employed, along with streptokinase.

Enzyme concentrations were determined by titration with nitrophenyl p-guanidinobenzoate in the case of trypsin, plasmin, and thrombin, whereas chymotrypsin molarity was based on weight. Kallikrein concentration is expressed in enzyme units as measured in a pH-state by esterase action on 0.02 M tos-Arg-OMe in 0.06 M KCl at pH 7.85; one unit corresponds to the hydrolysis of 1 μmole of ester per minute under these conditions.

The nitrophenyl esters were examined as possible substrates using a Beckman DB spectrophotometer with a temperature controlled cell compartment maintained at 25° C. and a recorder providing full scale deflection for 0.1 optical density unit. The ester was present in both reference and sample cells. Since the rate of hydrolysis of the p- and m-isomer at pH 8.3 is more rapid than that of nitrophenyl p-guanidino benzoate (NPGB), considerable care is required in pipetting aliquots, otherwise a level baseline is not obtained. Stock solutions of the p- and m-isomer ($10^{-2}$ M) in dimethyl formamide:$10^{-3}$ M HCl (4:1, v/v) were prepared and aliquots were diluted with 0.1 M sodium veronal buffer, pH 8.3, to provide a final concentration of isomer of $10^{-4}$ M (1% in DMF). In the case of trypsin and thrombin, $Ca^{2+}$, 0.02 M, was also present. The reactions were monitored for an increase of absorbance at 410 nm. To examine the reaction mixture for possible time-dependent loss of enzymatic activity, NPGB was, in some instances, added to the sample cuvette after several minutes of incubation to titrate residual enzyme.

Figure 1:
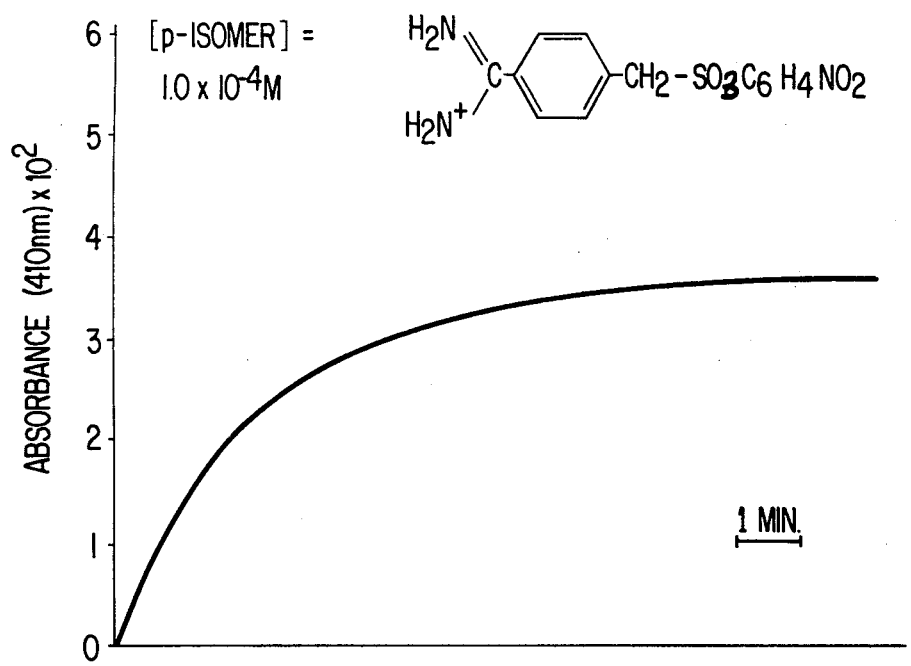
FIG. 1 is a graph showing stiochiometric nitrophenol release accompanying inactivation of thrombin by the use of the p-isomer of the present invention.

The action of thrombin on nitrophenyl p-amidinophenylmethanesulfonate was also studied in 0.05 M sodium veronal buffer, pH 7.4 (with 0.02 M $Ca^{2+}$ + at a series of reagent concentrations to determine the possible formation of an intermediate complex as a step in the inactivation process. The apparatus was the same as above and presteady state nitrophenol production was analyzed for the calculation of $k_2$ and $K_S$. Concentrations of the p-isomer were 0.5, 1.0, 2.0, 2.5, 3.75, and $5.0 \times 10^{-4}$ M. One of the progress curves is shown in FIG. 1, with this graph representing the action of thrombin ($3 \times 10^{-6}$ M) on the p-isomer, pH 8.3, 25° C., with stoichiometric nitrophenol release accompanying inactivation. Although the full chromogeneity of nitrophenol is not reached at this pH, the final value in each case was equal to that obtained in control titrations with NPGB.

To evaluate the nitrophenyl esters as competitive inhibitors, their effect on the cleavage of benzyloxy-lysine-nitrophenyl ester was determined in 0.2 M sodium maleate, pH 6.0. Optical density change at 340 nm was measured with double beam operation as described above. Dixon plots were constructed from hydrolysis rates of substrate at $10^{-4}$ M and $2.5 \times 10^{-5}$ M with plasmin ($1.03 \times 10^{-8}$ M), human thrombin ($2.0 \times 10^{-8}$ M), bovine thrombin ($2.3 \times 10^{-7}$ M), human plasma kallikrein (1.1 enzyme unit/ml), and chymotrypsin ($5 \times 10^{-7}$ M). In the case of trypsin ($1.56 \times 10^{-8}$ M), substrate concentrations of $4.17 \times 10^{-5}$ and $8.33 \times 10^{-5}$ M were employed. Since benzyloxy-lysine-nitrophenyl ester is not a typical substrate for chymotrypsin assay, it was established that its hydrolysis followed Michaelis-Menten kinetics in the concentration ranges examined, $0.67 \times 10^{-5}$ to $1 \times 10^{-4}$ M with a $K_m$ of $1.2 \times 10^{-5}$ M. The individual rate assays at the substrate concentrations used to obtain data for the Dixon plots were linear for at least 1 min. Anticoagulant assays were also caried out.

EXAMPLE 1

Chemical Reactivity of the Nitrophenyl Esters. A stock solution of each of the nitrophenyl esters ($10^{-2}$ M), including both the m- and p-isomers, were prepared and diluted 1 to 300 with 0.1 M borate buffer for hydrolyses carried out at pH 9.5 and 10 or with $10^{-2}$ M sodium hydroxide. In the latter case, the pH was measured for calculation of hydroxide ion concentration. The hydrolyses were followed to completion in a Gilford 2000 spectrophotometer recording O.D. change at 410 nm. Ester disappearance was calculated from the final value; intermediate points provided linear logarithmic plots from which an apparent first order constant was calculated.

EXAMPLE 2

Nitrophenyl p-Cyanophenylmethanesulfonate. The sodium salt of p-cyanophenylmethanesulfonic acid was prepared by refluxing α-bromo-p-tolunitrile (29.4 g) for 24 hr with sodium sulfite (20.2 g) in water (50 ml) with mechanical stirring. Following the addition of an equal volume of saturated aqueous NaCl, the mixture was cooled to room temperature. The crystalline sodium salt was filtered, washed with saturated NaCl and ether. It was dried at 110° C. for about 1 day prior to conversion to the sulfonyl chloride. The yield was 29.2 g, 61%.

The sodium salt (25.3 g) was refluxed with phosphorous oxychloride (50 ml) for 24 hr protected from moisture. After cooling, the mixture was filtered and the insoluble matter was washed with ether. The filtrates were combined and volatile material was removed at 40° C. under reduced pressure (15 min). The residue crystallized from ether and petroleum ether, providing 19.1 g (77%) of p-cyanophenylmethanesulfonyl chloride, m.p. 92°-95° C.

To a stirred solution of the sulfonyl chloride (8.5 g) in acetone (90 ml) was added p-nitrophenol sodium salt (8.5 g) and the reaction was allowed to proceed overnight (18 hr) at room temperature. The filtrate and an acetone wash were combined and evaporated to dryness under reduced pressure at 30° C. The residue was dissolved in chloroform (150 ml), washed with 5% NaHCO$_3$, 0.1 N HCl and distilled water and dried over sodium sulfate. The filtrate was concentrated until heavy crystallization, then 3 volumes of ethyl ether were added. The crystals were filtered and washed with ethyl ether, yielding 9.5 g (76%), m.p. 134°-136° C.

Anal. Calcd. for $C_{14}H_{10}N_2O_5S$: C, 52.82; H, 3.17; N, 8.80; Found: C, 52.72; H, 3.04; N, 8.83.

EXAMPLE 3

Nitrophenyl p-Amidinophenylmethanesulfonate. A solution of the nitrile produced in Example 2 (3.2 g) and anhydrous methanol (640 mg, 20 mmoles) in anhydrous tetrahydrofuran (35 ml) at 0° C. was saturated with a stream of anhydrous hydrogen chloride for 30 min, and the resultant solution was allowed to stand at 4° C. overnight. The product was precipitated with anhydrous ethyl ether (35 ml), filtered, washed thoroughly with ethyl acetate, and then immediately suspended in anhydrous methanol (40 ml). The methanolic suspension was titrated at 0° C. with methanolic ammonia until the solution began to turn yellow. The excess ammonia was immediately removed under reduced pressure in a rotary evaporator and the residue resuspended with stirring in methanol (40 ml) and heated at 60° C. for 3 hr. The reaction mixture was evaporated under reduced pressure until crystallization took place. The solid was collected by suction filtration and washed with ethyl acetate. A solution in acetone (40 ml) was filtered to remove some insoluble material and evaporated nearly to dryness in a rotary evaporator under reduced pressure. The crude product was completely precipitated with ethyl acetate (50 ml), filtered and dried in a desiccator under vacuum, yielding 2.2 g (59%).

The crude product (400 mg) was purified by addition to a solution of picric acid (1.0 g) in methanol (20 ml). Distilled water (4 ml) led to the crystallization of a picrate. After recrystallization from aqueous acetone, the yield was 330 mg, m.p. 211°–213° C.

Anal. Calcd. for $C_{20}H_{16}N_6O_{12}S$: C, 42.48; H, 3.03; N, 14.86; Found: C, 42.45; H, 2.77; N, 14.75.

For conversion to the hydrochloride, the picrate (320 mg) was dissolved in a minimum volume of acetone, treated with 2 volumes of 0.5 N HCl, and extracted thoroughly with toluene. The colorless aqueous layer was concentrated in a rotary evaporator at 30° C. until crystals formed and cooled at 0° C. The product was collected by suction filtration, washed with distilled water and ethyl acetate and dried, yielding 110 mg, m.p. 116°–118° C., thereafter resolidifying with a final m.p. at 181° C.

Anal. Calcd. for $C_{14}H_{14}N_3O_5ClS \cdot H_2O$: C, 43.13; H, 4.13; N, 10.78; Found: C, 43.03; H, 4.06, N, 10.76.

EXAMPLE 4

Nitrophenyl m-Amidinophenylmethanesulfonate. Using procedures described above for the p-isomer, α-bromo-m-tolunitrile was converted to sodium m-cyanophenylmethanesulfonate quantitatively. The sulfonyl chloride was obtained in 55% yield with m.p. 99°–101° C. and the nitrophenyl ester in 86% yield, m.p. 108°–109° C.

Anal. Calcd. for $C_{14}H_{10}N_2O_5S$: C, 52.82; H, 3.17; N, 8.80; Found: C, 52.77; H, 3.08; N, 8.75.

In the conversion to an amidine, 3 g of nitrile provided 2.1 g of crude product which was purified as the picrate, m.p. 210°–212° C.

Anal. Calcd. for $C_{20}H_{16}N_6O_{12}S$: C, 42.48; H, 3.03; N, 14.86; Found: C, 42.63; H, 2.87; N, 14.84.

The picrate (325 mg) was converted to the hydrochloride, m.p. 98°–99° C. (132 mg) by use of Dowex 1, Cl.

Anal. Calcd. for $C_{14}H_{14}N_3O_5ClS \cdot H_2O$: C, 43.13; H, 4.13; N, 10.78; Found: C, 43.05; H, 3.91; N, 10.93.

EXAMPLE 5

Nitrophenyl m- and p-Methylphenylmethanesulfonate. α-Chloro-p-xylene was converted to sodium p-methylphenylmethanesulfonate as described above and transformed via the sulfonyl chloride to the desired product, m.p. 119°–121° C.

Anal. Calcd. for $C_{14}H_{13}NO_5S$: C, 54.71; H, 4.26; N, 4.56; Found: C, 54.50; H, 4.11; N, 4.42.

The meta isomer, m.p. 113°–114° C., was also synthesized. Found: C, 54.69; H, 4.24; N, 4.47.

As a result of contacting various enzymes with the nitrophenyl esters of meta and para amidinophenylmethanesulfonic acid, it was found that the p-isomer, when exposed to trypsin, chymotrypsin, plasmin, and kallikrein, gave no evidence of nitrophenol release, that is, of substrate behavior. Thrombin, on the other hand, liberated nitrophenol in a manner indicating stoichiometric release with inactivation, as shown by FIG. 1, since at the new steady state no further nitrophenol production was evident and the color yield was equivalent to the thrombin content as established by titration with NPGB. The inactive state of the enzyme was demonstrated by the failure to produce a burst with this titrant. Furthermore, after removal of excess reagent by gel filtration, the thrombin remained in an inactive state for at least 48 hr; control samples of thrombin did not lose activity under the conditions used. The same results were obtained whether bovine or human thrombin was used.

Analysis of the presteady state kinetics at a series of concentrations of the p-isomer at pH 7.4 demonstrated the formation of a p-isomer-thrombin complex with a dissociation constant of $1.2 \times 10^{-4}$ M; the rate constant for inactive enzyme formation, $k_2$, was calculated to be 1.16 $\text{min}^{-1}$.

Figure 2:
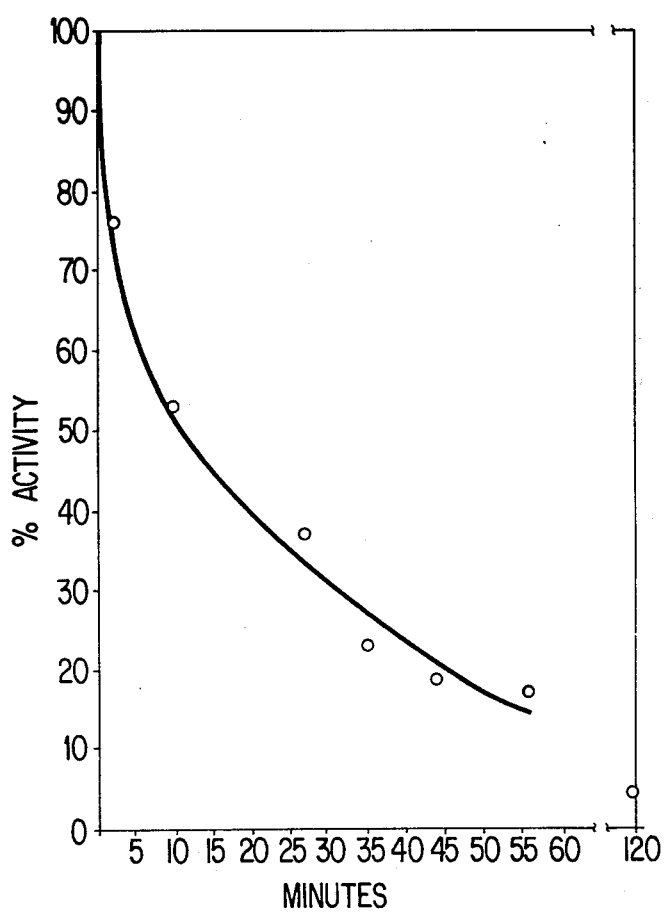
FIG. 2 is a graph showing anticoagulant action of the p-isomer on thrombin.

To confirm that thrombin was also inactivated with respect to its ability to act on fibrinogen, the action of the p-isomer was followed with a coagulation assay, as shown in FIG. 2. FIG. 2 represents anticoagulant action of the p-isomer at a concentration of $2 \times 10^{-5}$ M on thrombin ($2.6 \times 10^{-6}$M) at pH 7.38. A relatively low concentration of reagent was used to provide a slow inactivation permitting completion of these assays at intermediate points.

Thrombin appeared to have no effect on the meta isomer, in contrast to the above results, judging by the absence of nitrophenol release. Similar observations were made with trypsin, chymotrypsin, plasmin and plasma kallikrein. No loss of enzyme was found on titration.

Figure 3:
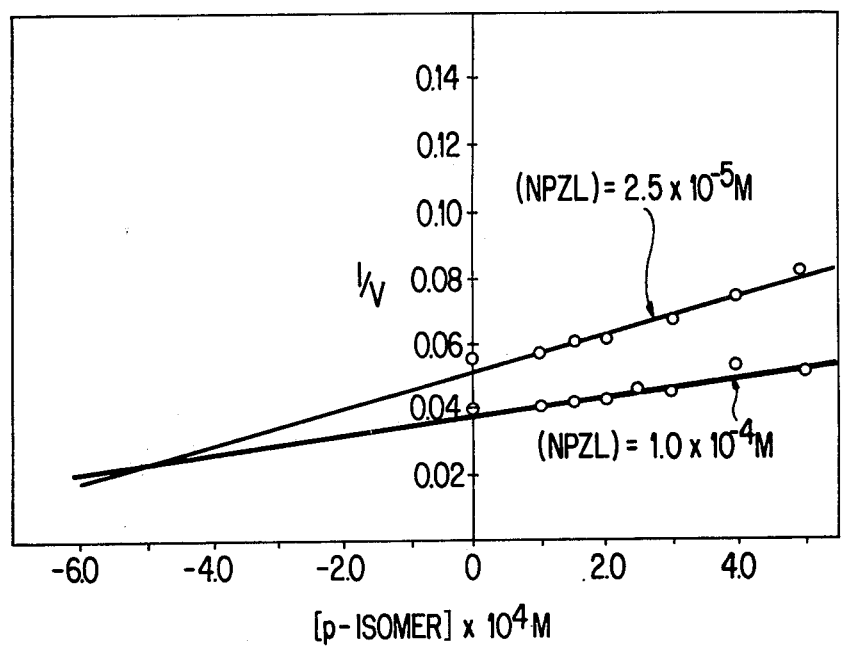
FIG. 3 is a graph showing competitive inhibition by the p-isomer of the esterase action of human plasmin.
Figure 4:
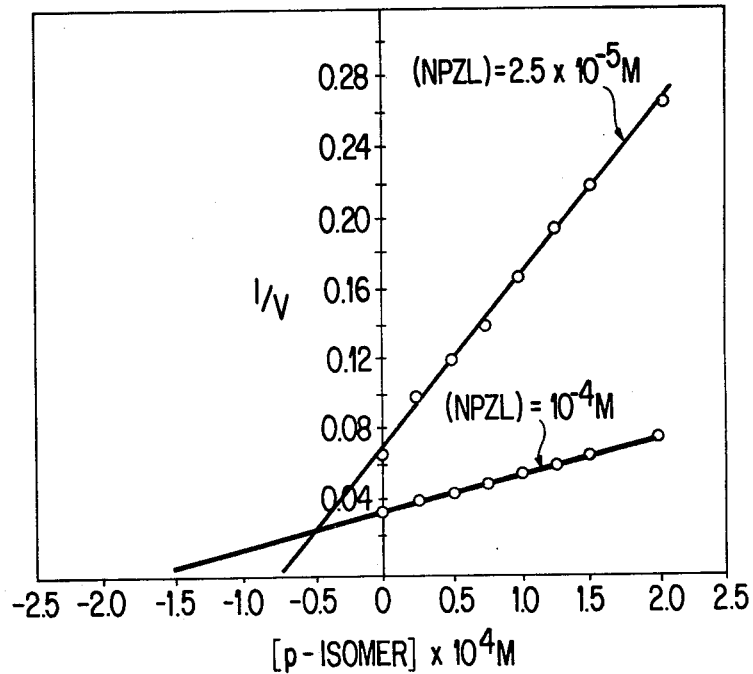
FIG. 4 is a graph showing competitive inhibition by the p-isomer of the esterase action of human plasma kallikrein.

The possibility that the p- and m-isomers have the ability to complex with the enzymes studied, although no esterase action was detectable, was examined by observing their effect on the enzymatic hydrolysis of nitro-phenyl $N^\alpha$-carbobenzyloxylysinate. Analysis by the method of Dixon, as described in *Biochem. J.*, 55, 170–171 (1953), indicated that the p- and m-isomers were competitive inhibitors of all the enzymes examined. The interaction of the p-isomer with plasmin and plasma kallikrein is shown in FIGS. 3 and 4. FIG. 3 shows the competitive inhibition by the p-isomer of the esterase action of human plasmin on nitrophenyl $N^\alpha$-benzyloxycarbonyl-lysinate (NPZL) at pH 6. FIG. 4 shows the competitive inhibition by the p-isomer of the esterase action of human plasma kallikrein on the same lysinate as in FIG. 3, also at pH 6. The graphically determined inhibition constants are given in Table I.

The positive charge in the p-isomer is essential for the inactivation of thrombin since its substitution by methyl resulted in a loss of biological activity.

Table I

INHIBITION CONSTANTS OF NITROPHENYL ESTERS I AND II DETERMINED FROM DIXON PLOTS

| Enzyme | I (p-isomer) | II (m-isomer) |
|---|---|---|
| | $K_i(M) \times 10^5$ | |
| β-Trypsin | 7.0 | 0.9 |
| α-Chymotrypsin | 3.6 | 1.3 |
| Thrombin (bovine) | (12)[a] | 41.5 |
| Thrombin (human) | | 5.3 |
| Plasmin (human) | 50 | 4.2 |
| Plasma kallikrein (human) | 4.7 | 1.9 |

[a]Determined from presteady state kinetics.

The results obtained, in accordance with the present invention, offer a remarkable example of selective inactivation of enzymes. The two reagents examined, the p- and m-isomer, are substrate analogs for trypsin-like enzymes and, in fact, form a complex with trypsin, thrombin, plasmin, and plasma kallikrein with $K_1$ values in the $10^{-4}$ to $10^{-5}$ M range. However, in only one case, i.e., the complex resulting from the p-isomer and thrombin, is the geometry favorable for a transfer of the sulfonyl group to the enzyme resulting in inactivation. It is clear that in spite of the structural homology prevailing among trypsin homologs, particularly in the region of the active center, that small variations exist which permit a qualitative difference in reactivity. Such a result is important from the point of view of chemotherapy since, although quantitative differences may be found among competitive inhibitors, with the p- and m-isomer and the trypsin homologs examined, as shown in Table I, these are not very great. On the other hand, considerably increased effectiveness of therapeutic agents apparently accompanies covalent combination to the target. Consequently, a qualitative difference in that property is very desirable.

The results concur with the generalization drawn from a review of affinity labeling that covalent modification does not correlate with affinity. Several of the enzymes complex more tightly to the p-isomer than does thrombin, as shown by Table I. In addition, the difference in response of thrombin to the p- and m-isomer cannot be related to differences in chemical reactivity since these are comparable, as shown in Table II. It is of interest that both isomers are considerably more reactive than a benzene sulfonate.

TABLE II

RATES OF ALKALINE HYDROLYSIS OF CERTAIN NITROPHENYL SULFONATES AT 250° C.

| Nitrophenyl | pH of experiment | $k_{2nd} \times 10^{-2}$ $min^{-1} M^{-1}$ |
|---|---|---|
| p-Amidinophenylmethanesulfonate | 9.5 | 73.3 |
| m-Amidinophenylmethanesulfonate | 9.5 | 34.4 |
| p-Methylphenylmethanesulfonate | 10.0 | 23.1 |
| m-Methylphenylmethanesulfonate | 10.0 | 16.1 |
| p-Methylbenzenesulfonate | 12.7 | 0.15 |
| p-Guanidinobenzoate | 8.3 | 0.45 |

The choice of nitrophenyl esters for inactivation of enzymes was based not only on their convenient spectroscopic properties, but also on the fact that alkyl sulfonates have a different mode of cleavage, acting as alkylating agents rather than sulfonylating. This property invites side reactions at sulfhydryl groups, certain to be encountered in in vivo situations; therefore it was considered desirable to avoid such a possibility in these initial studies. Also, it is believed that these esters are effective because of their substrate-like structure and the fact that they covalently combine at the active centers of susceptible enzymes, blocking their catalytic function.

In addition to the potential value of the p-isomer of the present invention as an anti-coagulant, its specificity provides a useful titrant for thrombin more selective, for example, than nitrophenyl p-guanidinobenzoate. This property should be of considerable assistance in a variety of experimental situations.

It is claimed:
1. p-Nitrophenyl p-amidinophenylmethanesulfonate.
2. p-Nitrophenyl m-amidinophenylmethanesulfonate.
3. The hydrochloride salt of the compound of claim 1.
4. The hydrochloride salt of the compound of claim 2.

* * * * *